United States Patent
Ceccoli et al.

(10) Patent No.: US 8,202,519 B2
(45) Date of Patent: Jun. 19, 2012

(54) MARINE EXTRACTS AND BIOFERMENTATIONS FOR USE IN COSMETICS

(75) Inventors: Joseph Ceccoli, Farmingville, NY (US); Brian Costello, Lake Grove, NY (US); Sreekumar Pillai, Wayne, NJ (US)

(73) Assignee: BASF Corporation, Florham Park, NJ (US)

( * ) Notice: Subject to any disclaimer, the term of this patent is extended or adjusted under 35 U.S.C. 154(b) by 100 days.

(21) Appl. No.: 12/442,769

(22) PCT Filed: Sep. 26, 2007

(86) PCT No.: PCT/US2007/020854
§ 371 (c)(1), (2), (4) Date: Oct. 21, 2009

(87) PCT Pub. No.: WO2008/039515
PCT Pub. Date: Apr. 3, 2008

(65) Prior Publication Data
US 2010/0047219 A1   Feb. 25, 2010

Related U.S. Application Data

(60) Provisional application No. 60/847,236, filed on Sep. 26, 2006.

(51) Int. Cl.
*A61K 36/00* (2006.01)
*A61K 35/00* (2006.01)
*A61K 8/02* (2006.01)

(52) U.S. Cl. ............... 424/195.17; 424/93.51; 424/115; 424/401

(58) Field of Classification Search .............. None
See application file for complete search history.

(56) References Cited

U.S. PATENT DOCUMENTS

| | | | |
|---|---|---|---|
| 3,342,612 A | * | 9/1967 | Foster et al. |
| 5,547,988 A | * | 8/1996 | Yu et al. |
| 6,063,915 A | | 5/2000 | Hansen et al. |
| 6,369,043 B1 | | 4/2002 | Sato et al. |
| 2004/0228875 A1 | | 11/2004 | Leclerc et al. |
| 2005/0089499 A1 | | 4/2005 | Moussou et al. |

OTHER PUBLICATIONS http://pendiva.com/seaweed/arcodiotheca_gaudichaudii/.
Seaweeds of the Pacific Northwest: "*Sarcodiotheca gaudichaudii*"; Downloaded from world wide web on Apr. 15, 2011.*
Penman, A et al. J. Chem. Soc., 1973; 19: 21: 2182-7. Carrageenans. IX. Methylation analysis of galactan sulphates from *Furcellaria gastigiata, Gigartina canaliculata, Gigartina chamissoi, Gigartina atropurpurea, Ahnfeitia durvillaei, Gymnogongrus furcellatus, Eucheuma isiforme, Eucheuma unicinatum, Aghardhiella tenera, Pachymenia hymantophora*, and.*
Witvrouw, M et al. Antiviral Chemistry and Chemotherapy, (1994) vol. 5, No. 5, pp. 297-303. Activity of a sulfated polysaccharide extracted from the red seaweed *Agardhiella tenera* against human immunodeficiency virus and other enveloped viruses.*
PCT Search Report, mailing date Aug. 29, 2008.
Whyte et al, 'Phycocolloid screening of British Columbia red algae'; Hydrobiologia, 1984, vol. 116/117, pp. 537-541; Dr. W. Junk Publishers, Dordrecht; Printed in the Netherlands.

* cited by examiner

*Primary Examiner* — Michele Flood
(74) *Attorney, Agent, or Firm* — Michelle J. Burke

(57) ABSTRACT

An extract of the marine algae, *Sarcodiotheca*, and more particularly *Sarcodiotheca gaudichaudii*, is described for use in cosmetic compositions. A biofermentation of *Sarcodiotheca*, such as for example *S. gaudichaudii*, is also described. This marine bioferment is useful as a skin care active ingredient for anti-aging cosmetic applications, and particularly useful when used in combination with an extracts of red algae, such as *Chondrus crispus*.

11 Claims, 3 Drawing Sheets

MARINE EXTRACTS AND BIOFERMENTATIONS FOR USE IN COSMETICS

TECHNICAL FIELD

The present invention relates to an extract of the marine algae, *Sarcodiotheca*, and more particularly *Sarcodiotheca gaudichaudii*, and its uses as a skin care active in cosmetic compositions. The invention also relates to a biofermentation of the *Sarcodiotheca*, such as for example *S. gaudichaudii*, useful as a skin care active for anti-aging cosmetic applications, and particularly useful when used in combination with an extracts of red algae, such as *Chondrus crispus*.

BACKGROUND ART

The extracellular matrix ("ECM") of the skin is extremely important in the aging process. Not only does the ECM provide the three-dimensional scaffolding needed for skin cell attachment and proper orientation of the skin, but the ECM also functions as the delivery conduit for the signals to skin cells which stimulate the cells to perform critical functions such as tissue repair. When the ECM is damaged, through environmental exposure or the normal aging process, the skin develops an undesirable aged appearance, such as wrinkling, due in part to the compromised structural integrity of fibrous proteins within the matrix, such as collagen or elastin. Thus, it is desirable to develop active ingredients, and cosmetics comprising such active ingredients, for reducing the damage to the existing fibrous proteins within the skin or alternatively, stimulating the production of more of these proteins. For example, human leukocyte elastase is a serine protease released by activated white blood cells and is capable of causing extensive damage to many of the ECM protein components, particularly elastin, in skin exposed to UV light or other irritant stimulus. Thus, it would be advantageous for a cosmetic to have an inhibitory effect on this protease in order to protect against damage to the ECM.

Numerous compounds have been described in the cosmetic field as being beneficial to the ECM or otherwise directed to delaying, minimizing or eliminating signs of aging or environmental damage to the skin. However, as increasing numbers of consumers begin to demand products that have a perceived "natural" origin, there is a continuing need to formulate cosmetic compounds using newly developed skin care actives based on plants and the like.

Marine plants, such as algae, have developed mechanisms and chemistries to protect and defend against the extreme environmental conditions of the sea, such as desiccation (high salt), solar radiation and high pressure, and have adapted to become capable of surviving in diverse marine environments. Algae can range from microscopic unicellular organisms to kelp seaweeds that exceed 100 meters in length, and are classified according to color—blue, red, green and brown. Many of these algae have both historically been and continue to be utilized for health and beauty as part of medicinal remedies, daily diets or dietary supplements, or cosmetics.

Surprisingly, it has been found that extracts and bioferments originating from the seaweed genus *Sarcodiotheca* provide anti-aging benefits when used as a skin care active in a cosmetic and applied to the skin, for example by inhibiting elastase and/or stimulating collagen production.

Thus, the present invention relates to marine extracts, particularly extracts of *Sarcodiotheca*, for use in cosmetic compositions to improve the condition of the skin and/or to provide anti-aging effects.

The present invention also relates to biofermentions (also referred to herein as "bioferments") of *Sarcodiotheca* for use in cosmetic compositions to improve the condition of the skin and/or to provide anti-aging effects, optionally mixed with extracts of other red algae or with human growth factor.

The present invention further relates to the cosmetic use of the described marine extracts and bioferments to stimulate collagen production and/or inhibit human leukocyte elastase in the skin.

Additionally, the present invention relates to the cosmetic use of the described marine extracts and bioferments to provide an antioxidant effect to the skin.

The present invention also relates to cosmetic compositions, such as gels, lotions or creams, comprising safe and effective amounts of the marine extracts and/or bioferments of the present invention.

These and other features and advantages of the present invention will become evident to those skilled in the art from a reading of the present disclosure.

DETAILED DESCRIPTION OF THE INVENTION

Figure 1:
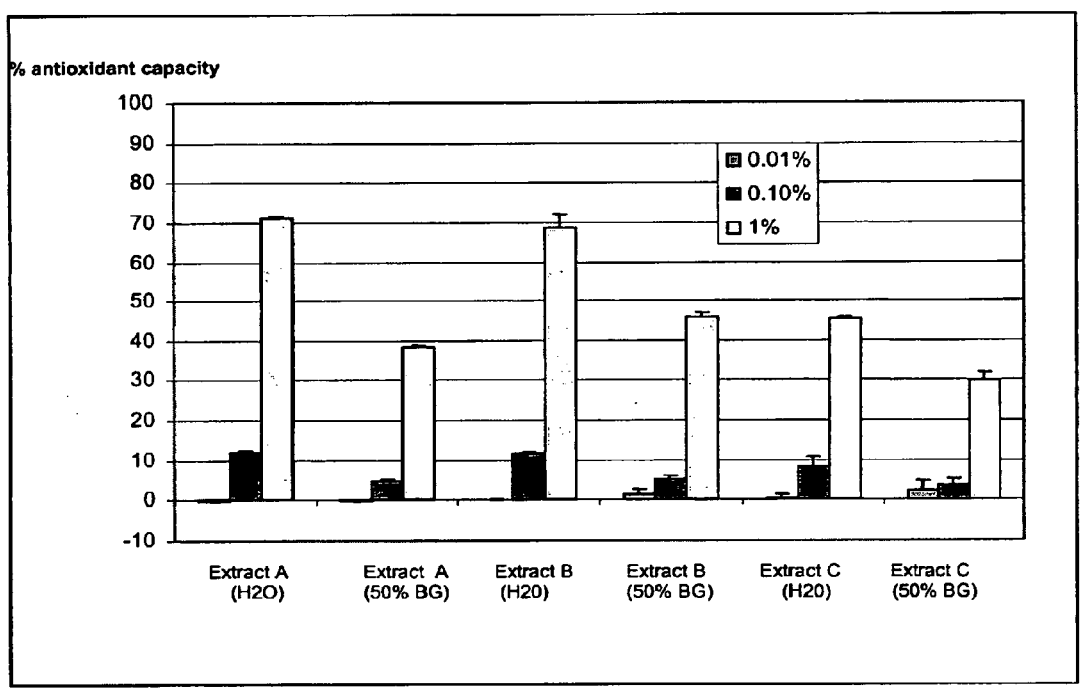
FIG. 1 is a graph of the test results of the ABTS Total Antioxidant Capacity Test of Example 4.

All percentages and ratios used herein are by weight of the total composition unless otherwise designated, and all temperatures are in degrees Celsius unless otherwise designated.

The term "safe and effective amount" as used herein means an amount of a compound or composition sufficient to induce a positive benefit as described herein, but low enough to avoid serious side effects in the judgment of the skilled artisan.

The term "slurry" as used herein means a suspension of plant matter in water.

As used herein, improving the condition of the skin includes diminishing, minimizing and/or preventing irregularities of the skin which can be detected visually or by feel, such irregularities including, but not limited to, wrinkles, unevenness or roughness, loss of skin elasticity, sagging, collagen breakdown, loss of skin recoil from deformation, and sallowness.

It has been unexpectedly found that seaweed extracts from the genus *Sarcodiotheca* provide anti-aging benefits when applied to the skin, particularly by acting as an antioxidant, an elastase inhibiting agent, and/or a collagen stimulating agent. These marine plants can be found, for example, along both the eastern and western coasts of the United States and Canada, but also along the coasts of England, Chile, Peru and elsewhere, and includes the following species: *S. caribaea, S. furcata, S. divaricata, S. gaudichaudii*, and *S. elongata*.

One particularly preferred species is *Sarcodiotheca gaudichaudii*. *S. gaudichaudii* is a medium to large species of flaccid red alga, with cylindrical, brittle fronds. The color can vary from straw yellow to a pale pink, deep red or reddish brown. It can be found in lower intertidal and upper subtidal pools, mainly on small stones and shells within sandy-mud habitats. Commonly referred to as "red string seaweed", *S. gaudichaudii* is sometimes made into a sweet desert in the Philippines.

The *Sarcodiotheca* used in the present invention may be natural occurring or cultivated. For industrial cosmetic applications, it is preferred to use cultivated *Sarcodiotheca* since cultivation reduces the risk that supplies will become limited as aquaculture expands and marine environmental conditions change. One particularly preferred method of cultivation is a hydroponic-type of cultivation. *Sarcodiotheca*, like all seaweeds, lack roots so true hydroponic cultivation in which plant roots are immersed in an aqueous nutrient solution cannot be utilized. However, an adaptation of traditional hydroponics is suitable to growing algae whereby algae growth is started from seed stocks which are then carefully maintained in large tanks into which sea water is pumped. This seawater may be filtered in order that it may be somewhat purified when it reaches the tanks, the amount of purification depending upon the filtration method and materials. Fertilizer or other forms of nutrients may be added to the water, and the nutrient levels can be monitored, resulting in a carefully controlled growth environment, such as with traditional hydroponically grown terrestrial plants. One particular benefit of this controlled growth environment is the ability to sustain growth and supply of naturally occurring genetic variants. Additionally, by adjusting the nutrient conditions (e.g., customization of the nutrient types and levels over time) during growth in this hydroponic type environment, it is possible to optimize the resulting seaweed plants for particular end uses, including the enhancement of any bioactivity and controlled selection thereof. Further, the controlled growth environment allows for the production of seaweeds having a consistent quality which is highly desirable for industrial applications such as cosmetics. Seaweeds cultivated in this manner are available commercially from suppliers, such as Acadian Seaplants Ltd of Dartmouth, Nova Scotia, Canada.

Once harvested, extracts of the *Sarcodiotheca* plants may be produced through any extraction method known by one skilled in the art. Particularly preferred extracts are aqueous extracts from dehydrated, whole plants. The amount of *Sarcodiotheca* utilized in any given extraction process will vary based on the methodology used and cost, but preferably ranges from about 1% to about 20%.

The *Sarcodiotheca* extracts are utilized in cosmetic compositions applied topically to produce anti-aging effects on the skin such as the inhibition of elastase and the stimulation of collagen. Additionally, the *Sarcodiotheca* extracts can be utilized to provide an antioxidant effect. The extracts of the present invention may be utilized in any form of cosmetic composition, whether in the cosmetic composition. The quantity of the extract should be a safe and effective amount for the desired benefit to be achieved and the type of composition (e.g., cream, gel, or lotion), but preferably the quantity of extract utilized ranges between 0.1% and 3%.

It was unexpected discovered that if *Sarcodiotheca* was fermented with a live culture of yeast to produce a bioferment, the potency of the *Sarcodiotheca*, particularly for the inhibition of elastase and/or stimulation of collagen, was substantially enhanced. Although the extract described above may be used, in one particularly preferred embodiment, water is added to dry *Sarcodiotheca* to produce a slurry of plant pulp and water, which is then added to a live culture of yeast. In one particularly preferred embodiment, *Saccharomyces cerevisiae* is used for the yeast culture. *Saccharomyces cerevisiae* is a well known and readily available species of budding yeast and the microorganism behind the most common type of fermentations. For the purposes of the present invention, the *S. cerevisiae* may be cultured by any conventional methods known to one skilled in the art. It is noted that similar fermentations of other red algae, such as *Chondus crispus*, did not demonstrate these enhanced inhibition and/or stimulation properties demonstrated by fermentations of *Sarcodiotheca*.

In one preferred embodiment, the bioferment of *Sarcodiotheca* is utilized between 0.01% to about 5% in a cosmetic formulation for increased collagen synthesis and elastase inhibition.

In one particularly preferred embodiment, an extract of red algae is mixed with the *Sarcodiotheca* bioferment and preserved to form a blend useful as a cosmetic active ingredient providing even more potent anti-aging effects. One preferred red algae species is *Chondrus crispus*, also commonly referred to as Irish moss or carrageen moss and often utilized in the cosmetic and food industries as a source for carrageen.

In one preferred embodiment, the bioferment and the red algae extract are blended at a 20:80 ratio. In yet another embodiment, the red algae extract and the bioferment are not blended as one active ingredient, but are used in combination within the formulation of a final cosmetic compound to provide enhanced anti-aging effects.

TGF-$\beta$1 (transforming growth factor beta-1) is a growth factor known to stimulate production of the ECM, it has been unexpectedly found that the *Sarcodiotheca* bioferment of the present invention may have a beneficial synergistic effect on the activity of endogenous TGF-$\beta$1 in the skin.

As specified previously, the extracts and bioferments of the present invention are particularly useful as active ingredients in cosmetic compositions. These cosmetic compositions can be processed in a conventional manner by one skilled in the art, and are suitable for cosmetic use. In particular, the compositions are preferably suitable for application to wrinkled, lined, rough, dry, flaky, aged and/or UV-damaged skin to improve the appearance and the feel thereof as well as for application to healthy skin to prevent or retard deterioration of the skin.

The cosmetic compositions of the present invention may further comprise various additives utilized in the cosmetic field. The CTFA Cosmetic Ingredient Handbook describes a wide variety of nonlimiting cosmetic ingredients commonly used by those skilled in the art and which are suitable for use in the cosmetic compositions of the present invention. Examples of these ingredient classes included: abrasives, emulsifiers, absorbents, gelling agents, antifoaming agents, buffering agents, colorants, film formers, pH adjusters, humectants, thickeners and pigments. It is further recognized that additional cosmetic active ingredients, such as anti-acne actives (for example, salicylic acid or benzoyl peroxide), anti-wrinkle actives (for example, retinoids or beta-hydroxy acids), antioxidants (for example, ascorbic acid and its derivatives or tea extracts), chelators (for example, furildioxime), anti-inflammatory agents (for example, corticosteroids), slimming agents (for example, caffeine), skin lightening agents (for example, mulberry extract or kojic acid), or sunscreens (for example, those commercially available under the name PARSOL), may be utilized in the cosmetic compositions of the present invention based on the desired overall benefits intended to be conferred by the composition.

The compositions of the present invention are generally prepared by conventional methods known in the art for making cosmetic compositions. Such methods typically involve mixing of the ingredients in one or more steps to a relatively uniform state, with or without heating, cooling, application of vacuum, or the like. The compositions may be in any conventional form, such as a gel, cream, lotion, or wash-off type product.

The upper and lower limits for the quantity of an extract or bioferment according to the present invention in any given formulation for a cosmetic composition is based both on the desired effect of the cosmetic compositions, the other components of the formulation, the type of composition, cost and practicality. However, the extract or bioferment preferably is included in a quantity between about 0.1% and about 5%, based on the final weight, more preferably between about 1% and 3%.

The cosmetic compositions described herein are particularly useful as part of method of cosmetic treatment for treating skin having signs of aging wherein such compositions are applied to skin in need of such treatment for the duration of time necessary to improve the condition of such skin. Although such duration of time will vary based on the efficacy of such cosmetic composition, it is preferred that the cosmetic composition be applied at least one a day to the skin.

The following examples further describe and illustrate the present invention and should not be construed as limitations of the present invention.

EXAMPLE 1

Dry samples of three *Sarcodiotheca* algae strains (all *Sarcodiotheca gaudichaudii* or variants thereof) were received from Acadian Seaplants Limited of Nova Scotia, Canada, and were rinsed with tap water and allowed to dry at room temperature. Extractions of the algae samples were made at 12.5% w/w in both 100% water and in 50% butylene glycol in water as vehicles. These extracts were prepared by shredding the sample in the vehicle and extracting at room temperature for 2 hours with mixing. The extracts were then vacuum-filtered using Whatman #1 paper (pore size ~11 μm) and the resulting extracts were stored at 4° C. These extracts are referred to in other examples herein as *Sarcodiotheca* extracts A, B, and C, based on which of the three algae strains were utilized.

EXAMPLE 2

*Sarcodiotheca* Bioferment

A slurry of 5% w/w dehydrated *Sarcodiotheca gaudichaudii* in water was prepared. The slurry was added to a live culture of *Saccharomyces cerevisiae* and incubated at room temperature for two days to complete the fermentation.

EXAMPLE 3

*Chondrus/Sarcodiotheca* Bioferment

A 5% w/w extract of *Chondrus crispus* was prepared from dry samples of the algae. A *Sarcodiotheca* bioferment was prepared in accordance with Example 2 and diluted. The *Chondus* extract and the *Sarcodiotheca* bioferment was mixed in an 80:20 ratio and filtered through a 0.1-0.3 μm filter.

EXAMPLE 4

Antioxidant Testing

The extracts of Example 1 were tested using the ABTS Total Antioxidant Capacity Test which measures the extent to which a given amount of a test sample scavenges an excess of the radical cation of ABTS (2,2'-azinobis-(3-ethylbenzothiazoline-6-sulfonic acid)). Results of the test are shown in FIG. 1. Any insoluble materials were removed from the samples by filtration (0.2 μm pore size) and/or centrifugation prior to testing. After testing was completed, a calculation was then performed to express this capacity in terms of the equivalent amount of the standard antioxidant Trolox (a water-soluble analog of α-tocopherol). This test is a standard method for determining the "total antioxidant capacity" of a test sample.

The test was performed by mixing aliquots of the extracts at varying concentrations into reaction mixtures containing a fixed amount of ABTS$^{\bullet+}$. At the end of a 20 minute reaction period, the remaining unscavenged ABTS$^{\bullet+}$ was determined by measuring its absorbance at 734 nm. Trolox is included as a sample in each assay as a standard for the purpose of expressing the test sample's antioxidant capacity in terms of its "Trolox equivalent". Specifically, the antioxidant capacity of each unknown is expressed in terms of the concentration (% v/v) that is equivalent to 20 μM Trolox. The Trolox equivalencies of the extracts are shown in Table 1 below. The samples with the lowest equivalent concentrations in Table 1 have the greatest scavenging capacity. The equivalent concentrations in Table 1 represent total scavenging capacity at endpoint (a thermodynamic parameter).

TABLE 1

| % v/v concentrations of test samples of seaweed extract that are equivalent to 200 uM Trolox in terms of ABTS radical Scavenging Capacity: | | |
|---|---|---|
| Sample | Water extract | 50% BG extract |
| *Sarcodiotheca* Extract A | 0.75 | 1.45 |
| *Sarcodiotheca* Extract B | 0.78 | 1.20 |
| *Sarcodiotheca* Extract C | 1.23 | 1.86 |

EXAMPLE 5

Leukocyte Elastase Inhibition Test

The *Sarcodiotheca* extracts of Example 1 were tested in a human leukocyte elastase inhibition test. Any insoluble materials were removed from the extracts by filtration (0.2 μm pore size) and/or centrifugation prior to testing. Positive activity in the test demonstrates anti-aging activity for the extract. The test was performed by following the rate of cleavage (optical density increase) of a chromogenic peptide substrate by human leukocyte elastase in the presence of varying concentrations of the test samples. The data are presented as the $IC_{50}$ value for each of the samples. The $IC_{50}$ is the concentration of test sample that inhibits human leukocyte elastase by 50%. Greater potency is indicated by a lower $IC_{50}$ value. The results of these tests are presented in Table 2 as the calculated $IC_{50}$ values.

TABLE 2

| IC 50 values for inhibition of Leukocyte elastase | | |
|---|---|---|
| Sample | Water extract | 50% BG extract |
| *Sarcodiotheca* A | 0.076 | >5 |
| *Sarcodiotheca* B | 0.018 | 0.9 |
| *Sarcodiotheca* C | 0.007 | 0.9 |

EXAMPLE 6

Collagen Stimulation Test

The *Sarcodiotheca* extract samples of Example 1 were tested in a type 1 collagen stimulation test. Any insoluble materials were removed from the samples by filtration (0.2 μm pore size) and/or centrifugation prior to testing. Dry samples of three *Chondrus crispus* strains were received from Acadian Seaplants Limited of Nova Scotia, Canada, and aqueous *Chondrus* extracts were prepared for comparison purposes using the same extraction methodology as for the *Sarcodiotheca* extracts (e.g., 12.5% w/w in 100% water) of Example 1. Human dermal fibroblast cells were grown to confluence in multiwell plates and then stimulated with varying concentrations of both the *Sarcodiotheca* and *Chondrus* extracts. After incubation for 3 days, the amount of type 1 collagen that was secreted into the growth medium was measured by ELISA. The amount of collagen present under each test condition is expressed as a percentage of that detected in the medium from unstimulated cells. Results of this test for the aqueous extracts are shown in Table 3 below. Toxic concentrations of the samples are indicated by the symbol "--" in the Table below.

TABLE 3

Collagen stimulation by aqueous extracts of *Sarcodiotheca* and *Chondrus*

| | Collagen Production expressed as % of unstimulated control +/− SE Test Concentration (% v/v) | | | | | |
|---|---|---|---|---|---|---|
| Algae Samples | 0.01 | 0.03 | 0.1 | 0.3 | 1.0 | 3.0 |
| *Sarcodiotheca* extract A | N/A | N/A | 215 +/− 14 | 283 +/− 19 | 256 +/− 15 | — |
| *Sarcodiotheca* extract B | 189 +/− 30 | 226 +/− 31 | 250 +/− 28 | 209 +/− 20 | — | — |
| *Sarcodiotheca* extract C | 210 +/− 22 | 272 +/− 16 | 260 +/− 24 | — | — | — |
| *Chondrus* extract A | N/A | 131 +/− 13 | 162 +/− 25 | 215 +/− 27 | 265 +/− 25 | 259 +/− 33 |
| *Chondrus* extract B | N/A | N/A | 142 +/− 14 | 181 +/− 14 | 231 +/− 20 | 229 +/− 12 |
| *Chondrus* extract C | N/A | 155 +/− 10 | 227 +/− 19 | 276 +/− 19 | 312 +/− 11 | 274 +/− 12 |

Samples were tested in triplicate wells and mean±SE (standard error of mean) was calculated. In all cases (except 0.03% v/v *Chondrus* extract A) p values for non-toxic concentrations were less than 0.01 indicating significant stimulation of collagen synthesis.

EXAMPLE 7

Algae Extracts, Algae Extract/Yeast Extract Combinations & Algae/Yeast Ferments

The following samples were tested for the two anti-aging activities, elastase inhibition and stimulation of collagen production, as the extracts of Examples 5 and 6 above.
1. 5% w/w aqueous extracts of *Sarcodiotheca* and *Chondrus* algae
2. 20% of the 5% seaweed extracts+80% yeast extract (*Sarccharomyces cerevisae*)
3. 20% of the 5% seaweed slurry+80% of live yeast (*Sarccharomyces cervical*) incubated for 2 days The extracts were prepared using conventional extraction methods from samples of the marine algae, *Chondrus* and *Sarcodiotheca*, and the yeast, *Sarccharomyces cerevisiae*. A culture of *Sarccharomyces cerevisiae* was also prepared using conventional methods. After extraction and incubation, the samples were filtered using Whatman 1 micron filter paper and further clarified using 0.8 and 0.2 micron filtration. The filtrates were tested for elastase inhibition and collagen stimulation pursuant to the methodologies discussed in Examples 5 and 6.

Inhibition of Leukocyte Elastase

Results are summarized in Table 4 below.

TABLE 4

| | IC 50 values for inhibition of Leukocyte elastase: | | |
|---|---|---|---|
| Algae sample | 5% w/w extract | 20% of 5% extract + 80% yeast extract | 20% of the 5% extract + 80% live yeast |
| *Chondrus* | 2.8-5 | 5.4 | 15-20 |
| *Sarcodiotheca* | 0.8-1.0 | 8.0 | 0.45-0.9 |

In general, the *Chondrus* extracts showed low elastase inhibitory activity and there was no benefit from fermentation or when used in combination with the yeast extract. However, for *Sarcodiotheca*, there was a substantial increase in the elastase inhibitory activity for the extract upon fermentation with live yeast. Fermentation increased the activity of the *Sarcodiotheca* extract by up to 20 times. In contrast, when diluted with the 80% yeast extract the activity was very low indicating that the yeast broth (dead yeast extract) had no elastase inhibitory activity.

Collagen Stimulation Test

Results are summarized in Tables 5 below.

| | Collagen Production expressed as % of unstimulated control +/− SE Test Concentrations (% v/v) | | | | | |
|---|---|---|---|---|---|---|
| Algae Sample | 0.01 | 0.03 | 0.1 | 0.3 | 1.0 | 3.0 |
| *Sarcodiotheca* 5% w/w extract | 118 +/− 18 | 108 +/− 13 | 98 +/− 8 | 199 +/− 16 | 229 +/− 9 | 65 +/− 4 |
| *Sarcodiotheca* 20% of 5% extract + 80% yeast extract | 94 +/− 6 | 108 +/− 13 | 106 +/− 15 | 104 +/− 8 | 127 +/− 15 | 132 +/− 16 |
| *Sarcodiotheca* 20% of 5% slurry + 80% live yeast culture | 180 +/− 40 | 198 +/− 45 | 238 +/− 57 | 198 +/− 61 | 352 +/− 75 | 237 +/− 51 |
| *Chondrus* 5% extract | 108 +/− 14 | 119 +/− 19 | 141 +/− 19 | 195 +/− 16 | 176 +/− 18 | 155 +/− 9 |

-continued

| | Collagen Production expressed as % of unstimulated control +/− SE Test Concentrations (% v/v) | | | | | |
|---|---|---|---|---|---|---|
| Algae Sample | 0.01 | 0.03 | 0.1 | 0.3 | 1.0 | 3.0 |
| *Chondrus* 20% of 5% extract + 80% yeast extract | 136 +/− 20 | 123 +/− 16 | 97 +/− 6 | 149 +/− 19 | 150 +/− 17 | 133 +/− 9 |
| *Chondrus* 20% of 5% slurry + 80% live yeast | 116 +/− 15 | 127 +/− 18 | 224 +/− 12 | 181 +/− 22 | — | — |

Among the *Chondrus* samples, the ferment (slurry+live yeast) showed modest collagen stimulation activity and the 5% w/w extract and the extract diluted with yeast extract showed very minimal activity. Among the *Sarcodiotheca* samples, the ferment (slurry+live yeast) showed very good collagen stimulation activity. For example, 1% of this ferment increased collagen synthesis by as much as 350% of control. The extract diluted with yeast extract showed no activity. In summary, as in the case of elastase inhibition activity, *Sarcodiotheca* activity was enhanced by the fermentation process, while the fermentation process failed to enhance the activity of *Chondrus* extract.

EXAMPLE 8

Blend of *Sarcodiotheca* Bioferment with *Chondrus* Extract

A *Chondus/Sarcodiotheca* bioferment was prepared as follows: A 0.67% w/w extract of *Chondrus crispus* was prepared from dry samples of the algae. A slurry of 0.056% w/w dehydrated *Sarcodiotheca gaudichaudii* in water was prepared. The slurry was added to a live culture of *Saccharomyces cerevisiae* and incubated at room temperature for two days to complete the fermentation. The *Chondus* extract and the *Sarcodiotheca* bioferment was mixed in an 80:20 ratio and filtered through a 0.1-0.3 µm filter and further diluted.

Leukocyte Elastase Inhibition Test

The test was performed as described in Example 5 for varying concentrations of the *Chondus/Sarcodiotheca* bioferment. The results are shown in Table 6 below.

TABLE 6

| Leukocyte Elastase Inhibition | |
|---|---|
| *Chondus/Sarcodiotheca* Bioferment (% v/v) | Human Leukocyte elastase inhibition (% inhibition) |
| 0 | 0 |
| 2 | 24 |
| 4 | 41 |
| 6 | 50 |
| 8 | 54 |
| 10 | 58 |
| 15 | 60 |

Collagen Stimulation Testing

Tests were performed as described in Example 6. The assay used 2 samples: one that had been stored continuously at 4° C., and an aliquot that was switched to 40° C. for the week preceding the 3-day cell stimulation. Table 7 (error bars are one SE) below show the collagen content, as percentages of untreated control cultures, for the 4° C. and 40° C. samples.

TABLE 7

| Collagen Stimulation | | |
|---|---|---|
| *Chondus/Sarcodiotheca* Bioferment (% v/v) | 4° C. storage samples | 40° C. storage samples |
| 0.3 | 198 +/− 40 | 222 +/− 18 |
| 1.0 | 225 +/− 36 | 260 +/− 35 |
| 3.0 | 148 +/− 16 | 245 +/− 28 |

Figure 3:
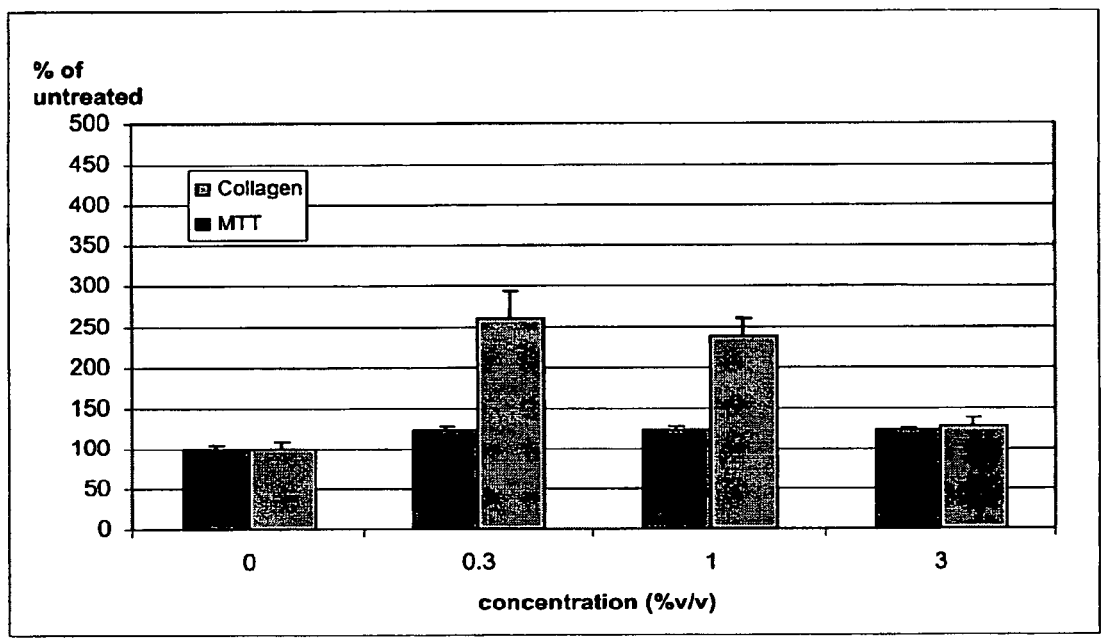
FIG. 3 is a graph of the test results shown in Table 7.

Additional samples at all concentrations were stored 40° C. for the 6 weeks preceding the 3-day cell stimulation. The results of stimulating cells is shown in FIG. 3. It was found that the efficacy of IH2837 for collagen stimulation increased further when storage at 40 C was extended to 6 weeks.

EXAMPLE 9

*Sarcodiotheca* Bioferment and Growth Factor

Figure 2:
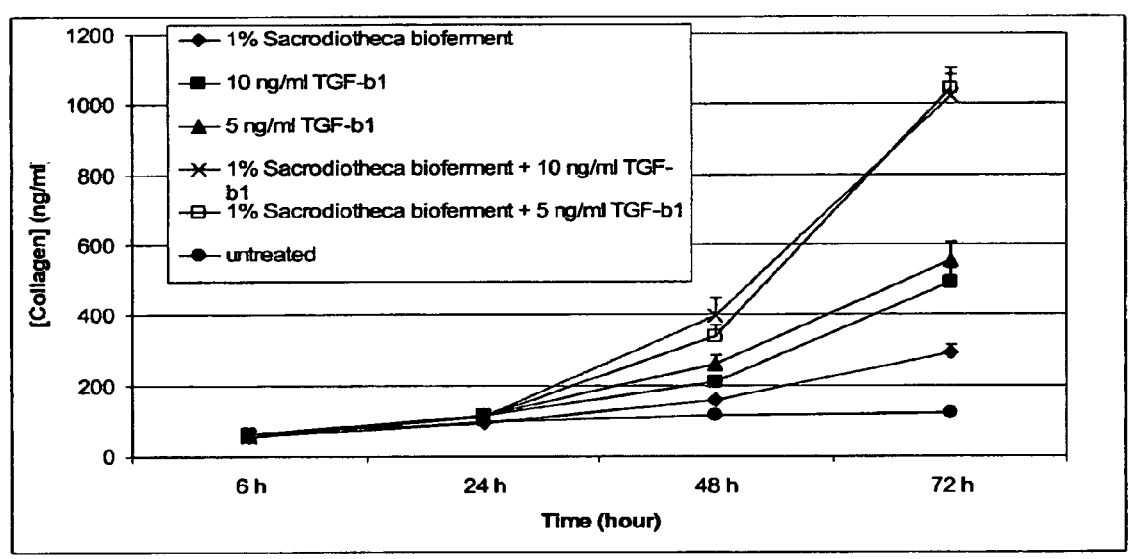
FIG. 2 is a graph of the test results shown in Table 8.

Collagen production by a *Sarcodiotheca* bioferment of the present invention and by TGF-β1, alone and in combination, were tested. The *Sarcodiotheca* bioferment was prepared as described herein Normal human dermal fibroblasts were grown for 3 days in the presence of these two effectors. The levels of soluble type I collagen were measured in the supernatant media by enzyme-linked immunosorbent assay (ELISA). Media were collected at several timepoints following initiation of stimulation. The results are shown in Table 8 and FIG. 2, wherein it can be seen that collagen levels increased under all conditions, but that the levels in the cultures treated by the *Sarcodiotheca* bioferment plus TGF-µ1 were greater than the sum of their individual effects. This is a synergistic effect showing that *Sarcodiotheca* bioferment is able to accentuate the beneficial effect of a natural endogenous growth factor.

TABLE 8

| Sample | 6 h (mean) | 24 h (mean) | 48 h (mean) | 72 h (mean) |
|---|---|---|---|---|
| 1% Sarco bioferment | 54 | 95 | 159 | 294 |
| 10 ng/ml TGF-b1 | 61 | 117 | 208 | 491 |
| 5 ng/ml TGF-b1 | 62 | 116 | 259 | 553 |
| 1% Sarco bioferment + 10 ng/ml TGF-b1 | 55 | 114 | 397 | 1023 |
| 1% Sarco bioferment + 5 ng/ml TGF-b1 | 55 | 113 | 338 | 1043 |
| untreated | 62 | 99 | 115 | 123 |

EXAMPLE 10

Cosmetic Compositions

The following examples illustrate skin care compositions according to the present invention. The compositions can be processed in a conventional manner, and are suitable for cosmetic use.

This example illustrates an anti-aging cream according to the present invention.

| Ingredients | % w/w |
| --- | --- |
| *Sarcodiotheca* bioferment | 2.0 |
| Butylene glycol | 3.0 |
| Disodium EDTA | 0.05 |
| Penulan TR2* | 0.1 |
| Carbowax PEG 400** | 5.0 |
| Montanov 68**** | 5.0 |
| Mineral Oil | 5.0 |
| Protachem CER*** | 5.0 |
| Preservative blend | 1.5 |
| Water | to 100 |

*from Noveon;
**from Dow Chemicals;
***from Protameen;
****from Seppic.

This example illustrates an oil-in-water cream according to the present invention.

| Ingredients | % w/w |
| --- | --- |
| *Chondrus/Sarcodiotheca* bioferment | 2.0 |
| Mineral oil | 4.0 |
| 1,3-dimethyl-2-imidazolidinone | 1.0 |
| Alfol ® 16RD* | 4 |
| Triethanolamine | 0.75 |
| Butane-1,3-diol | 3 |
| Xanthan gum | 0.3 |
| Perfume | qs |
| Butylated hydroxy toluene | 0.01 |
| Water | to 100 |

*Alfol 16RD is cetyl alcohol and is a registered trademark of Condea Vista Co.

This example illustrates a face rinse off lotion/gel composition according to the invention.

| Ingredients | % w/w |
| --- | --- |
| *Sarcodiotheca* bioferment | 2.0 |
| Antioxidant (vitamin C) | 2 |
| Butylene glycol | 5.0 |
| Preservative | 1.0 |
| Simulgel EPG | 2.5 |
| Biowax 754 liquid | 5.0 |
| Glycerin | 6.0 |
| Perfume | qs |
| Carbopol 980 | 0.5 |
| Water | to 100 |

This example illustrates a composition for an anti-aging cream according to the invention:

| Ingredients | % w/w |
| --- | --- |
| Butylene Glycol (1) | 5.00 |
| Glycerin (2) | 3.00 |
| *Sarcodiotheca* bioferment | 1.50 |
| Polymethylmethacrylate (Microma 100, Ikeda) | 2.00 |
| Cetearyl Alcohol and Polysorbate 60 and PEG-150 Stearate and Steareth-20 | 4.50 |
| Stearyl Heptanoate | 4.50 |
| Cetyl Recinoleate | 4.50 |
| Hydrogenated Polyisobutene | 3.00 |
| Isononyl Isononanoate | 1.30 |
| Synthetic Beeswax (Synthetic Beeswax #122P, Koster Keunen) | 1.75 |
| Hydroxyethyl Acrylate/Sodium Acryloyldimethyl Taurate Copolymer and Squalane and Polysorbate 60 | 1.00 |
| Cyclomethicone (DC345, Dow Corning) | 1.00 |
| Dimethicone (DC200/100, Dow Corning) | 0.2 |
| Tetrahexyldecyl Ascorbate | 0.25 |
| Preservative (Phenoxyethanol (and) Chlorphenesin (and) Glycerin (and) Methylparaben (and) Benzoic Acid) | 1.20 |
| Deionized Water | 1.5 |
| Ascorbyl Glucoside | 0.25 |
| Deionized Water | to 100 |

This example illustrates an alcoholic lotion according to the invention.

| Ingredients | % w/w |
| --- | --- |
| *Chondrus/Sarcodiotheca* bioferment | 1.5 |
| 1,3-dimethyl-2-imidazolidinone | 0.01 |
| Ethanol | 40 |
| Antioxidant | 0.1 |
| Perfume | qs |
| Water | to 100 |

This example illustrates a non-aqueous skin care composition according to the invention.

| Ingredients | % w/w |
| --- | --- |
| *Chondrus/Sarcodiotheca* bioferment | 2 |
| 1,3-dimethyl-2-imidazolidinone | 1 |
| Silicone gum SE-30 | 10 |
| Silicone fluid 345 | 20 |
| Silicone fluid 344 | 50.26 |
| Squalene | 10 |
| Linoleic acid | 0.01 |
| Cholesterol | 0.03 |
| 2-hydroxy-n-octanoic acid | 0.7 |
| Herbal oil | 0.5 |
| Ethanol | 2 |

This example illustrates a sunscreen composition with SPF 15 according to the invention.

| Ingredient | % w/w |
| --- | --- |
| Acrylates/C10-30 Alkyl Acrylate Crosspolymer (Pemulen TR-2, Protameen) | 0.120 |

-continued

| Ingredient | % w/w |
|---|---|
| *Sarcodiotheca* bioferment | 1.0 |
| Butylene Glycol | 3.000 |
| Polymethylmethacrylate (Microma 100, Kobo) | 1.000 |
| Hydroxyethylacrylate/Sodium Acryloyldimethyl Taurate Copolymer (and) Squalane (and) Polysorbate 60 (Simulgel NS, Seppic) | 1.250 |
| Ethylhexyl Methoxycinnamate | 7.500 |
| Octyl Salicylate | 5.000 |
| Caprylic/Capric Triglyceride | 3.000 |
| Hydrogenated Polyisobutene | 5.000 |
| Pentaerythrityl Tetraisononanoate (Pelemol P49, Phoenix) | 0.500 |
| Acetylated Glycol Stearate (Cetacene, Vevy) | 2.000 |
| Cetearyl Alcohol (and) Ceteareth-20 (Phoenoxol T, Phoenix) | 3.000 |
| Octocrylene | 4.000 |
| Cetearyl Alcohol (and) Coco-Glucoside | 3.000 |
| Butyl Methoxydibenzoylmethane | 3.000 |
| Dimethicone (Silicone HL-88, Barnet) | 2.500 |
| Preservatives (Phenoxyethanol (and) Chlorphenesin (and) Glycerin (and) Methylparaben (and) Benzoic Acid) | 1.250 |
| Deionized water | to 100 |

It should be understood that the specific embodiments of the invention herein illustrated and described are intended to be representative only, as the invention may be modified and practiced in different but equivalent manners apparent to those skilled in the art having the benefit of the teachings herein. It is therefore evident that the particular embodiments disclosed above may be altered or modified and all such variations are considered within the scope and spirit of the invention.

The invention claimed is:

1. A cosmetic ingredient comprising a ferment of *Sarcodiotheca* obtained by fermenting a slurry of *Sarcodiotheca* pulp and water with a live yeast culture.

2. The cosmetic ingredient of claim 1 wherein the *Sarcodiotheca* is *Sarcodiotheca gaudichaudii*.

3. The cosmetic ingredient of claim 1 wherein the yeast culture comprises *Saccharomyces cerevisiae*.

4. A cosmetic composition comprising the cosmetic ingredient of claim 1 and at least one cosmetically acceptable additive.

5. The composition of claim 4 further comprising a second extract of red algae.

6. The composition of claim 5 wherein the red algae is *Chondrus crispus*.

7. The cosmetic ingredient of claim 1 further comprising adding a *Chondrus* extract to the ferment of *Sarcodiotheca* to form a blend of the ferment and the *Chondrus* extract.

8. The cosmetic ingredient of claim 7 wherein the ratio of *Chondrus* extract to the *Sarcodiotheca* ferment is 80:20.

9. The cosmetic ingredient of claim 7 further comprising at least one cosmetically acceptable additive.

10. A method for improving a condition of aging skin comprising applying to skin in need thereof an effective amount of the composition of claim 4.

11. A method for improving a condition of aging skin comprising applying to skin in need thereof an effective amount of the composition of claim 9.

* * * * *